US012751610B2

(12) United States Patent

Ikeda et al.

(10) Patent No.: US 12,751,610 B2
(45) Date of Patent: Oct. 6, 2026

(54) ENDOSCOPE CLEANING CART

(71) Applicant: NATIONAL UNIVERSITY CORPORATION EHIME UNIVERSITY, Matsuyama (JP)

(72) Inventors: Yoshio Ikeda, Toon (JP); Kunihiro Fujimoto, Toon (JP); Rumiko Moriwaki, Toon (JP)

(73) Assignee: NATIONAL UNIVERSITY CORPORATION EHIME UNIVERSITY, Matsuyama (JP)

( * ) Notice: Subject to any disclaimer, the term of this patent is extended or adjusted under 35 U.S.C. 154(b) by 431 days.

(21) Appl. No.: 18/549,678

(22) PCT Filed: Mar. 4, 2022

(86) PCT No.: PCT/JP2022/009450
§ 371 (c)(1),
(2) Date: Sep. 8, 2023

(87) PCT Pub. No.: WO2022/196395
PCT Pub. Date: Sep. 22, 2022

(65) Prior Publication Data

US 2024/0148241 A1 May 9, 2024

(30) Foreign Application Priority Data

Mar. 18, 2021 (JP) ................................ 2021-044685

(51) Int. Cl.
*A61B 1/12* (2006.01)
*A61B 50/20* (2016.01)
*A61B 90/70* (2016.01)

(52) U.S. Cl.
CPC ................ *A61B 1/12* (2013.01); *A61B 50/20* (2016.02); *A61B 90/70* (2016.02); *A61B 2090/701* (2016.02)

(58) Field of Classification Search
CPC ........... A61B 1/12; A61B 50/20; A61B 90/70; A61B 2090/701; A61B 1/121; A61B 50/13
See application file for complete search history.

(56) References Cited

U.S. PATENT DOCUMENTS 3,578,774 A * 5/1971 McDonald, Jr. .... A61M 3/0241 604/153
2015/0068939 A1* 3/2015 Seitz, III ............ A61M 25/002 206/363

(Continued)

FOREIGN PATENT DOCUMENTS

CN 1578679 A * 2/2005 ............... A61L 2/26
CN 1610517 A * 4/2005 ......... A61B 1/00144

(Continued)

OTHER PUBLICATIONS

English translation of DE102014017397 (Year: 2016).*

(Continued)

*Primary Examiner* — Regina M Yoo
(74) *Attorney, Agent, or Firm* — Alleman Hall LLP

(57) ABSTRACT

The present invention provides a cart that can perform bedside cleaning and carry an endoscope, and carries the endoscope, and carries an endoscope including an insertion unit to be inserted into a body cavity and an operation unit for operating the insertion unit, the cart including: a placement portion on which a storage bag storing a cleaning liquid is placed; and a holding portion that holds the operation unit above the placement portion, in which the operation unit is held by the holding portion, and the insertion unit is immersed in the cleaning liquid in the storage bag.

7 Claims, 13 Drawing Sheets

(56) References Cited

U.S. PATENT DOCUMENTS

| | | | | | |
|---|---|---|---|---|---|
| 2015/0069728 | A1 * | 3/2015 | Seitz, III | ............... | A61M 25/00 206/305 |
| 2015/0257632 | A1 | 9/2015 | Ramsey | | |

FOREIGN PATENT DOCUMENTS

| | | | | | | |
|---|---|---|---|---|---|---|
| CN | 102941196 | B | * | 1/2016 | ............... | A61L 2/18 |
| CN | 210872044 | U | * | 6/2020 | | |
| CN | 211534344 | U | | 9/2020 | | |
| CN | 111743505 | A | | 10/2020 | | |
| CN | 111759466 | A | * | 10/2020 | ............. | A61B 50/13 |
| DE | 102014017397 | A1 | * | 5/2016 | ............. | A61B 1/126 |
| ES | 2246471 | T3 | * | 2/2006 | ............. | A61B 90/70 |
| JP | H05095888 | A | | 4/1993 | | |
| JP | H07111981 | A | | 5/1995 | | |
| JP | H10258018 | A | * | 9/1998 | | |
| JP | 2004267764 | A | | 9/2004 | | |
| JP | 2005323944 | A | | 11/2005 | | |
| JP | 2009118882 | A | | 6/2009 | | |
| JP | 2011143179 | A | * | 7/2011 | ............. | A61B 1/122 |
| JP | 2015536194 | A | | 12/2015 | | |
| JP | 2016150064 | A | | 8/2016 | | |
| JP | 2016214787 | A | | 12/2016 | | |
| WO | 2014072706 | A1 | | 5/2014 | | |

OTHER PUBLICATIONS

English translation of JP2011143179 (Year: 2011).*

English translation of CN210872044 (Year: 2020).*

European Patent Office, Extended European Search Report Issued in Application No. 22771149.6, Oct. 12, 2024, Germany, 11 pages.

“Polyoxymethylene,” Wikipedia Website, Available Online at https://en.wikipedia.org/w/index.php?title=Polyoxymethylene&oldid=965749573, Website Available as Early as Jul. 3, 2020, retrieved on Nov. 25, 2024, 8 pages.

ISA Japan Patent Office, International Search Report Issued in Application No. PCT/JP2022/009450, May 24, 2022, WIPO, 6 pages.

China National Intellectual Property Administration, Office Action and Search Report Issued in Application No. 202280020553.6, May 23, 2026, 14 pages.

* cited by examiner

FRONT VIEW

REAR VIEW

RIGHT SIDE VIEW

LEFT SIDE VIEW

PLAN VIEW

BOTTOM VIEW

ENDOSCOPE CLEANING CART

TECHNICAL FIELD

The present invention relates to an endoscope cleaning cart.

BACKGROUND ART

As a cart for carrying a conventional endoscope, as disclosed in Patent Literature 1, a medical electric device loading cart capable of safely and cleanly handling an endoscope at the time of moving to an endoscope room, storage, or the like is considered. The medical electric device loading cart includes a scope hanger that holds an endoscope, and includes at least one of a heating unit that raises the temperature around the endoscope held by the scope hanger, a heat retaining unit that retains the temperature around the endoscope at a preset temperature, and a drying unit that removes moisture around the endoscope.

On the other hand, the Safety Management Committee of the Japan Gastroenterological Endoscopy Technician Society recommends bedside cleaning in which the endoscope is cleaned immediately after removal from the body cavity of the patient.

However, the medical electric device loading cart described in Patent Literature 1 is intended to keep the endoscope in an appropriate state until the time of use, and does not consider bedside cleaning after use at all. As described above, in the cart that carries the conventional endoscope, the endoscope before use is safely and cleanly handled, and how to handle the endoscope after use including bedside cleaning is not considered.

CITATION LIST

Patent Literature

Patent Literature 1: JP 5-95888 A

SUMMARY OF INVENTION

Technical Problem

The present invention has been made in view of the above-described problems, and a main object thereof is to provide a cart capable of performing bedside cleaning and carrying an endoscope.

Solution to Problem

That is, an endoscope cleaning cart according to the present invention carries an endoscope including an insertion unit to be inserted into a body cavity and an operation unit for operating the insertion unit, and includes: a placement portion on which a storage bag storing a cleaning liquid is placed; and a holding portion that holds the operation unit above the placement portion, in which the operation unit is held by the holding portion, and the insertion unit is immersed in the cleaning liquid in the storage bag.

With such an endoscope cleaning cart, it is possible to efficiently perform the bedside cleaning of the endoscope by causing the holding portion to hold the operation unit of the endoscope immediately after removal from the body cavity of the patient and immersing the insertion unit in the cleaning liquid in the storage bag. In addition, since the endoscope after use can be carried to the cleaning chamber in this state, it is possible to safely carry the endoscope after use and to efficiently clean the endoscope in the cleaning chamber.

As a specific embodiment of the holding portion, it is desirable that the holding portion includes one or a plurality of hanger portions for hooking the operation unit.

With this configuration, it is only necessary to hook the operation unit on the hanger portion, and the operation of holding the operation unit can be simplified.

In the case of a configuration having a plurality of hanger portions, there is a possibility that the operation units hooked on the hanger portions interfere with each other and are hardly hooked or become unstable after being hooked. In order to solve this problem, it is desirable that the plurality of hanger portions are configured such that the operation units adjacent to each other are alternately arranged in a state where the plurality of operation units are hooked.

It is desirable that the holding portion is formed of a material having translucency.

With this configuration, it is easy to understand whether or not dirt remains on a less visible portion (for example, the back surface) of the holding portion after the endoscope cleaning cart is cleaned, and the holding portion can be kept clean.

In order to prevent the insertion unit from being damaged in a state of being immersed in the cleaning liquid in the storage bag, it is desirable that a cushion member is provided below the storage bag in the placement portion.

The storage bag may be damaged by the insertion unit, and the cleaning liquid may leak from the storage bag. Therefore, it is desirable that the endoscope cleaning cart according to the present invention further includes a leakage preventing box that is provided between the storage bag and the placement portion and stores a lower portion of the storage bag.

In order to facilitate cleaning of the leakage preventing box, it is desirable that the leakage preventing box is set with a leakage preventing bag that stores the lower portion of the storage bag, and is detachably provided from the placement portion.

It is desirable that the endoscope cleaning cart of the present invention further includes a handle portion gripped at the time of carrying and provided on a rear side in a traveling direction, and the handle portion and the holding portion are provided on the same side.

With this configuration, since the holding portion is provided on the same side as the handle portion, the endoscope can be stabilized at the time of carrying.

It is desirable that the endoscope cleaning cart of the present invention further includes: an upper frame portion to which an upper portion of the storage bag is attached; and a connecting frame portion provided between the upper frame unit and the placement portion, and a space is formed between the upper frame portion and the placement portion.

With this configuration, the storage bag and the inside thereof can be visually recognized from between the upper frame and the placement portion, and the state of the insertion unit of the endoscope and the like can be confirmed.

Advantageous Effects of Invention

According to the present invention described above, it is possible to provide the cart capable of performing bedside cleaning and carrying the endoscope.

DESCRIPTION OF EMBODIMENTS

An endoscope cleaning cart according to an embodiment of the present invention will be described with reference to the drawings.

Note that any of the following drawings is schematically omitted or exaggerated as appropriate for easy understanding.

<Device Configuration>

Figure 1:
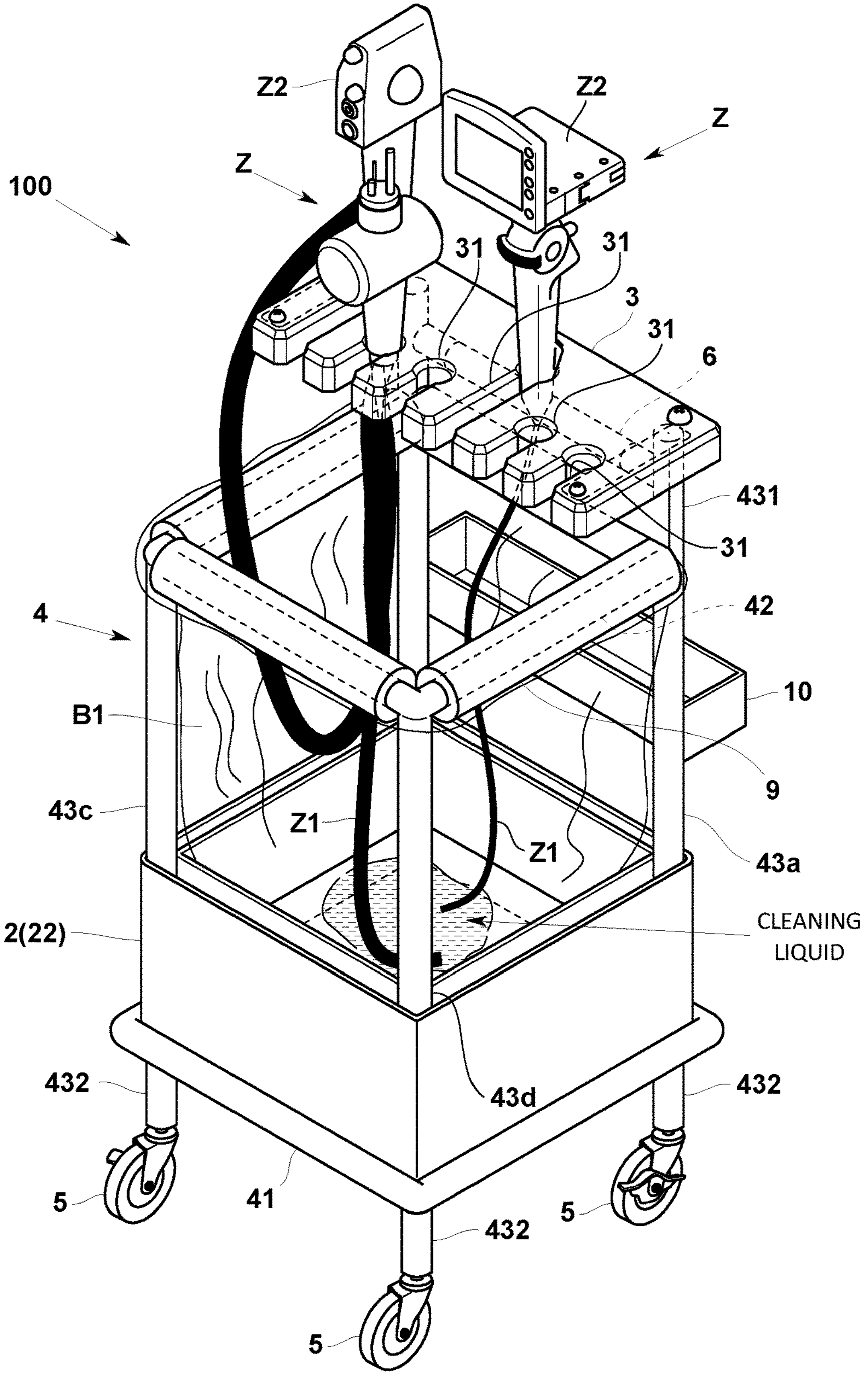
FIG. 1 is a perspective view illustrating a usage state of an endoscope cleaning cart according to an embodiment of the present invention.
Figure 2:
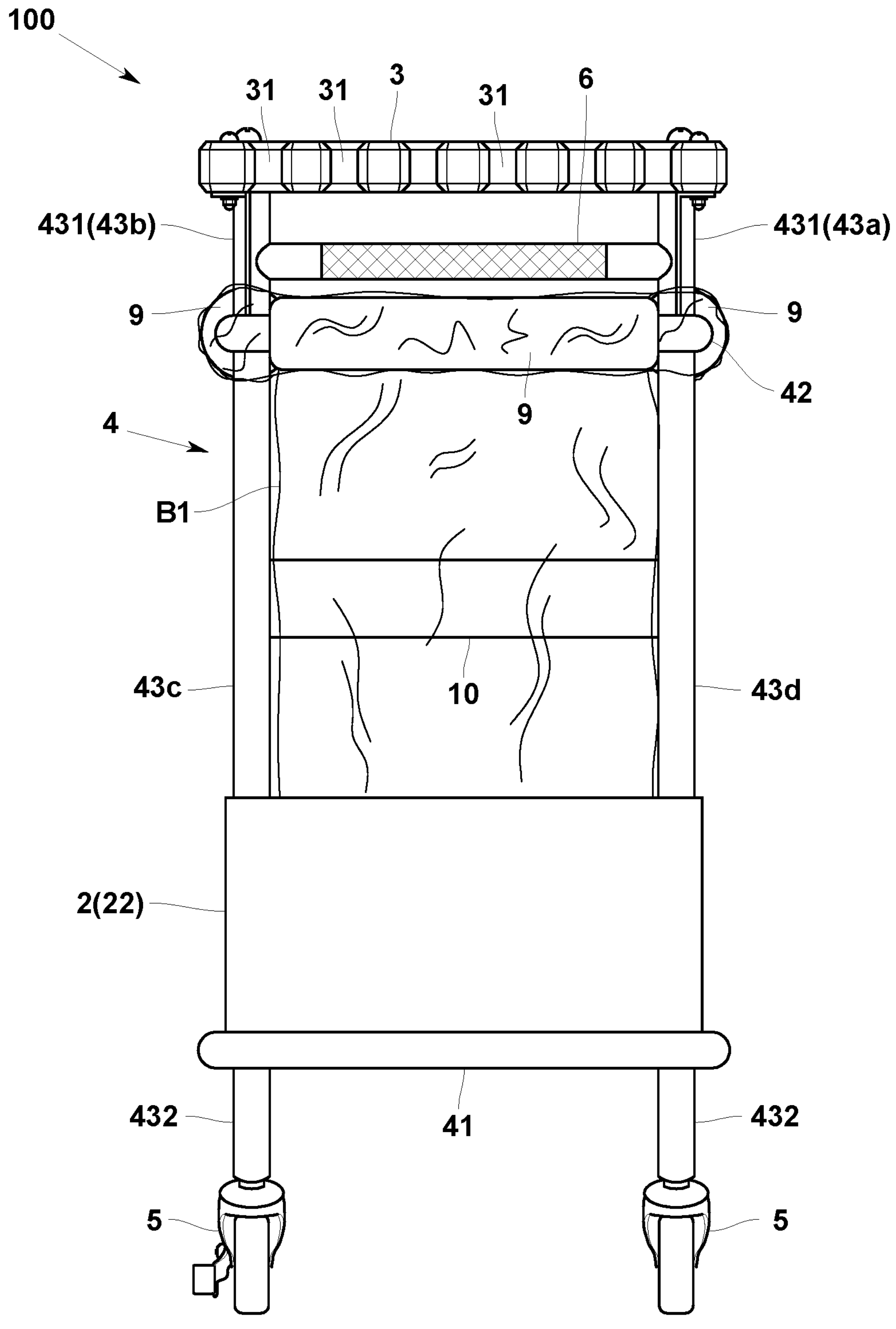
FIG. 2 is a front view of the endoscope cleaning cart of the embodiment.
Figure 3:
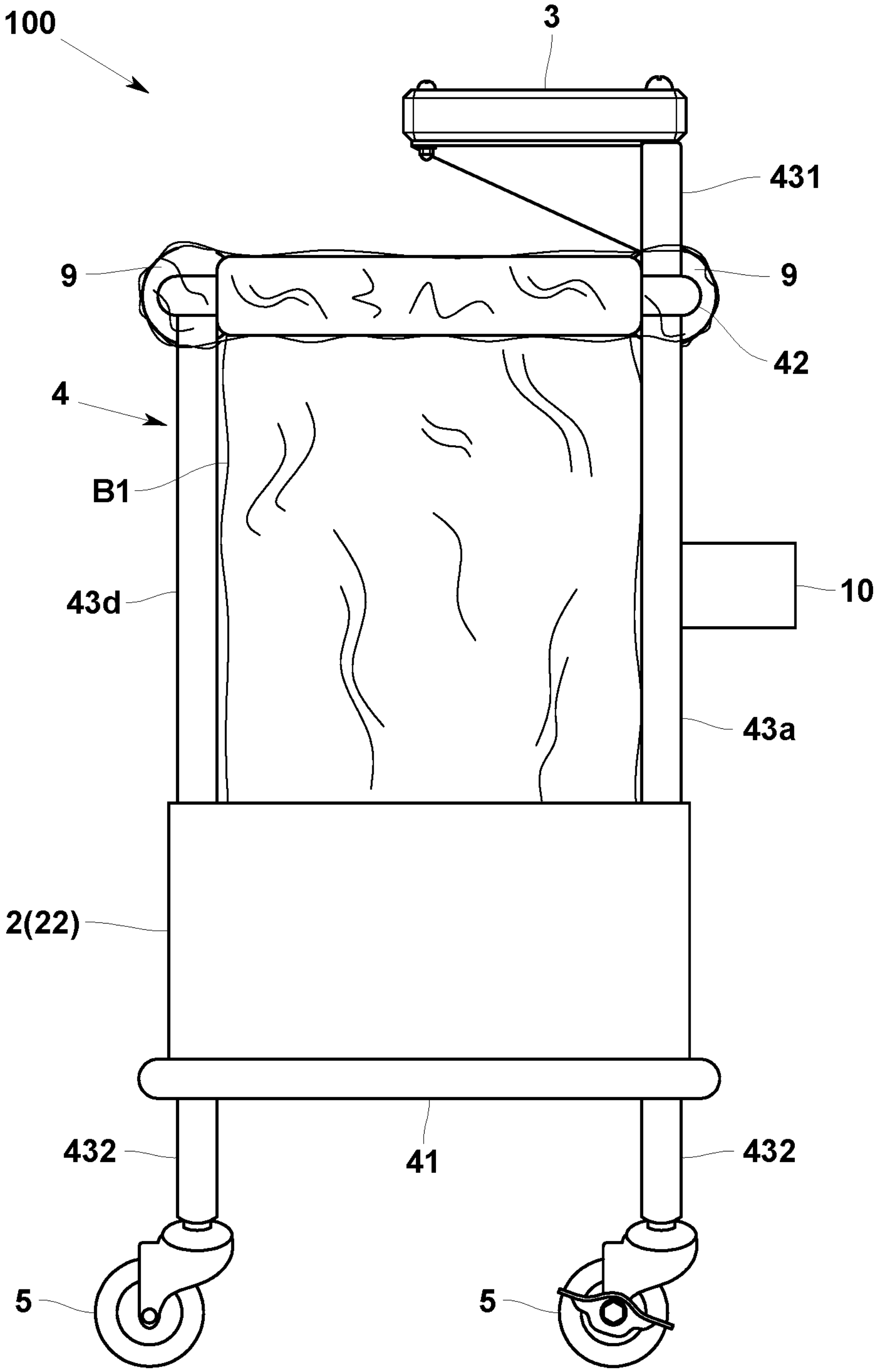
FIG. 3 is a side view of the endoscope cleaning cart of the embodiment.
Figure 4:
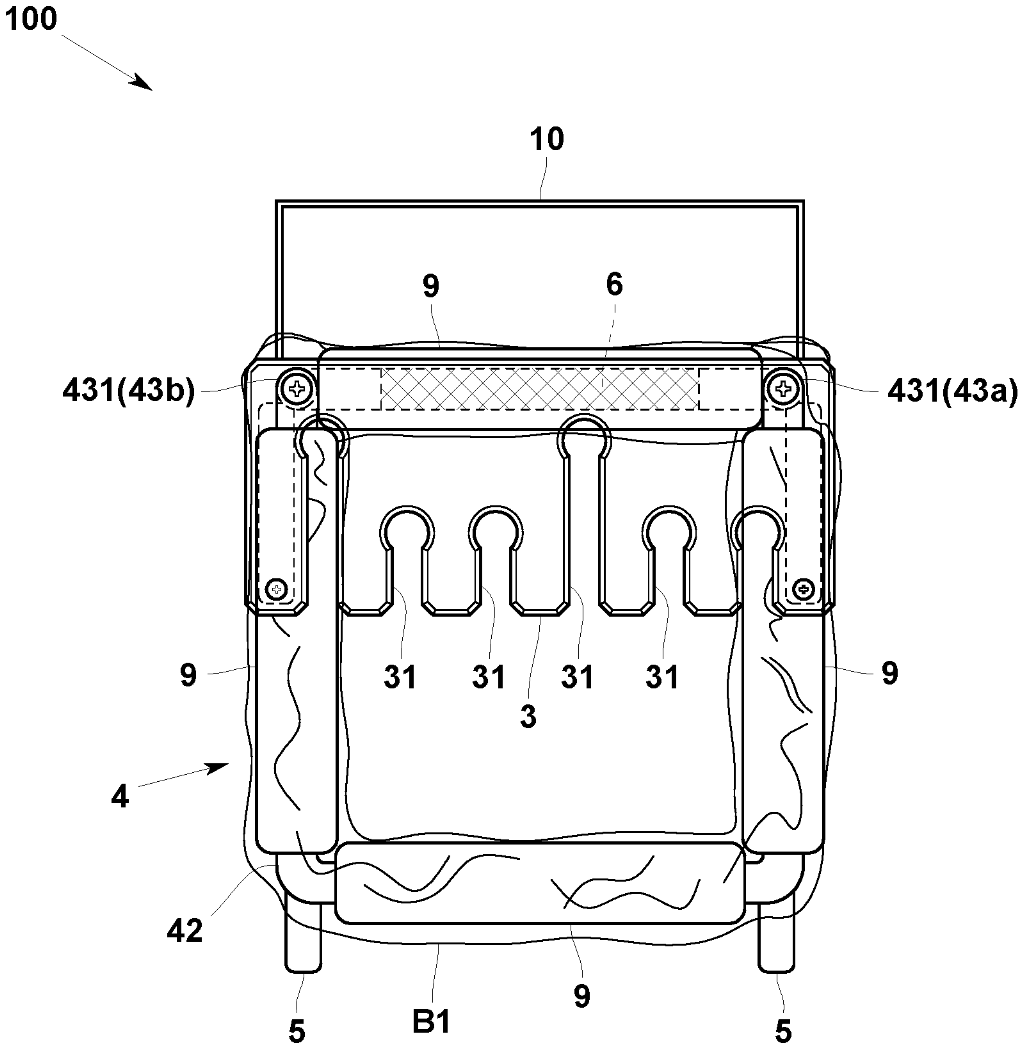
FIG. 4 is a plan view of the endoscope cleaning cart of the embodiment.

As illustrated in FIG. 1, an endoscope cleaning cart 100 of the present embodiment carries an endoscope Z after use from, for example, an endoscopic examination room to a cleaning room. Furthermore, the endoscope cleaning cart 100 is used to perform bedside cleaning of the endoscope Z after use, for example, in the endoscopic examination room. Note that the endoscope Z includes an insertion unit Z1 to be inserted into a body cavity and an operation unit Z2 for operating the insertion unit Z1. Although FIG. 1 illustrates two types of endoscopes (normal endoscope and portable flexible endoscope with display such as for airway management), the type of endoscope is not limited thereto.

Specifically, as illustrated in FIGS. 1 to 4, the endoscope cleaning cart 100 includes a placement portion 2 on which a storage bag B1 storing a cleaning liquid is placed, and a holding portion 3 that holds an operation unit Z2 above the placement portion 2. In the endoscope cleaning cart 100 of the present embodiment, the placement portion 2 and the holding portion 3 are provided on the cart main body 4 having a substantially rectangular parallelepiped frame shape.

The cleaning liquid is, for example, an enzyme cleaning agent for cleaning the insertion unit Z1. In addition, for example, a transparent plastic bag can be used as the storage bag B1 in order to make the inside visible.

In a lower portion of the cart main body 4, casters 5 are provided at four corners, respectively. In addition, the cart main body 4 is gripped at the time of carrying and has a handle portion 6 provided on the rear side in the traveling direction.

The cart main body 4 includes a lower frame portion 41 having a rectangular frame shape on which the placement portion 2 is provided, an upper frame portion 42 having a rectangular frame shape on which an upper portion of the storage bag B1 storing the cleaning liquid is attached, and linear connecting frame portions 43*a* to 43*d* that connect the lower frame portion 41 and the upper frame portion 42 and are provided between the upper frame portion 42 and the placement portion 2.

In the cart main body 4, at least the upper frame portion 42 is covered with a buffer member 9 made of resin such as urethane, for example, in order to prevent the endoscope Z (in particular, the insertion unit Z1) from coming into contact with and being damaged. Note that the cart main body 4 is made of stainless steel in consideration of durability and rust prevention.

Further, in the cart main body 4, the connecting frame portions 43*a* and 43*b* on the handle portion 6 side have upper extending portions 431 extending upward from the upper frame portion 42, and the handle portion 6 is provided so as to connect the upper extending portions 431. The holding portion 3 is provided on the upper portion of the upper extending portion 431. That is, the handle portion 6 and the holding portion 3 are provided on the same side (the rear side in the traveling direction) in the cart main body 4. The connecting frame portions 43*a* to 43*d* have lower extending portions 432 extending downward from the lower frame portion 41, and casters 5 are provided on the lower extending portion 432.

Figure 5:
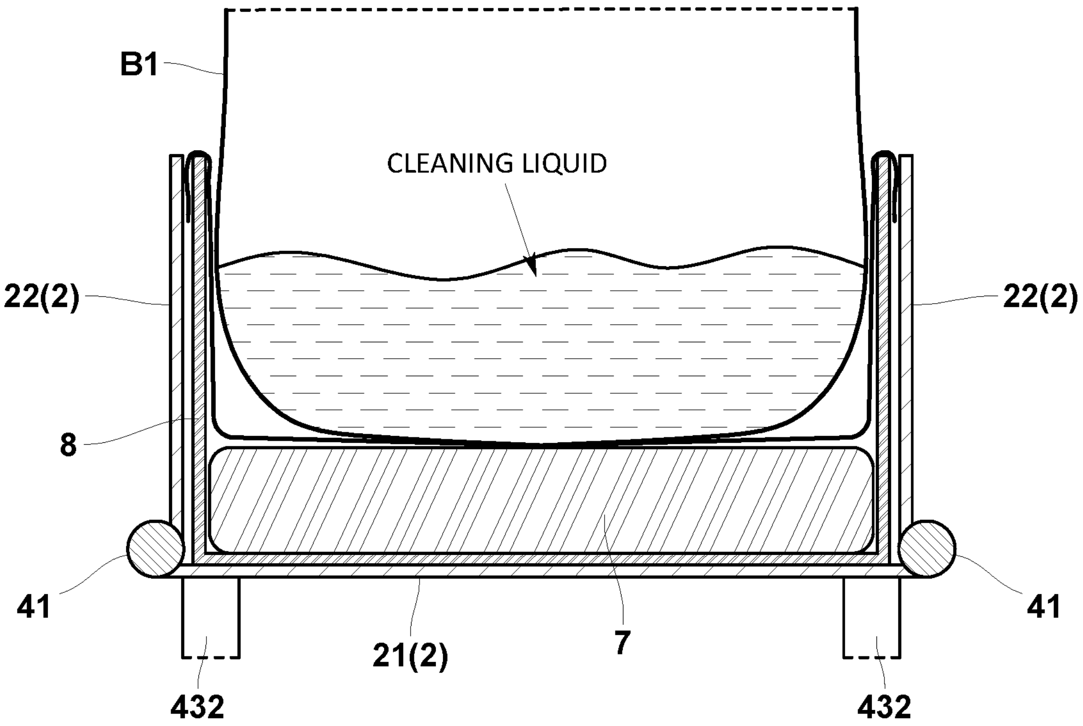
FIG. 5 is a cross-sectional view of a placement portion and a leakage preventing box of the same embodiment.

The placement portion 2 is provided in the lower frame portion 41 of the cart main body 4, and the storage bag B1 storing the cleaning liquid is placed thereon. As illustrated in FIG. 5, the placement portion 2 of the present embodiment includes, for example, a planar placement surface portion 21 on which the storage bag B1 is placed on the upper surface, and a side wall portion 22 surrounding the placement surface portion 21 so that the storage bag B1 placed on the placement surface portion 21 does not fall outward from the placement surface portion 21.

The side wall portion 22 is provided over the connecting frame portions 43*a* to 43*d* adjacent to each other, and is provided continuously with the placement surface portion 21 in the present embodiment. The placement surface portion 21 and the side wall portion 22 form a storage space opened upward, and the lower portion (portion storing the cleaning liquid) of the storage bag B1 is stored in the storage space. In this configuration, there is a space between the upper frame portion 42 and the placement portion 2, specifically, between the upper frame portion 42 and the side wall portion 22.

As illustrated in FIG. 5, a cushion member 7 made of, for example, resin is provided below the storage bag B1 in the placement portion 2. In the present embodiment, since a leakage preventing box 8 is provided between the storage bag B1 and the placement portion 2, the cushion member 7 is provided at the bottom portion of the leakage preventing box 8.

The leakage preventing box 8 stores a lower portion of the storage bag B1, and is configured to be detachable from the placement portion 2. Specifically, the leakage preventing box 8 is detachably stored in a storage space including the placement surface portion 21 and the side wall portion 22.

A leakage preventing bag B2 for storing a lower portion of the storage bag B1 is detachably set in the leakage preventing box 8.

Furthermore, a pocket portion 10 is provided in the connecting frame portions 43*a* and 43*b* on the handle portion 6 side in the cart main body 4. The pocket portion 10 stores an air/water supply adapter used at the time of cleaning, a waterproof cap at the time of replacing the air/water supply adapter, a contaminant container, a tool used at the time of cleaning a bucket or the like, or a tool necessary for other operation. The pocket portion 10 is provided so as to bridge the connecting frame portions 43*a* and 43*b* on the handle portion 6 side, and is fixed behind the connecting frame portions 43*a* and 43*b* in the traveling direction.

Figure 6:
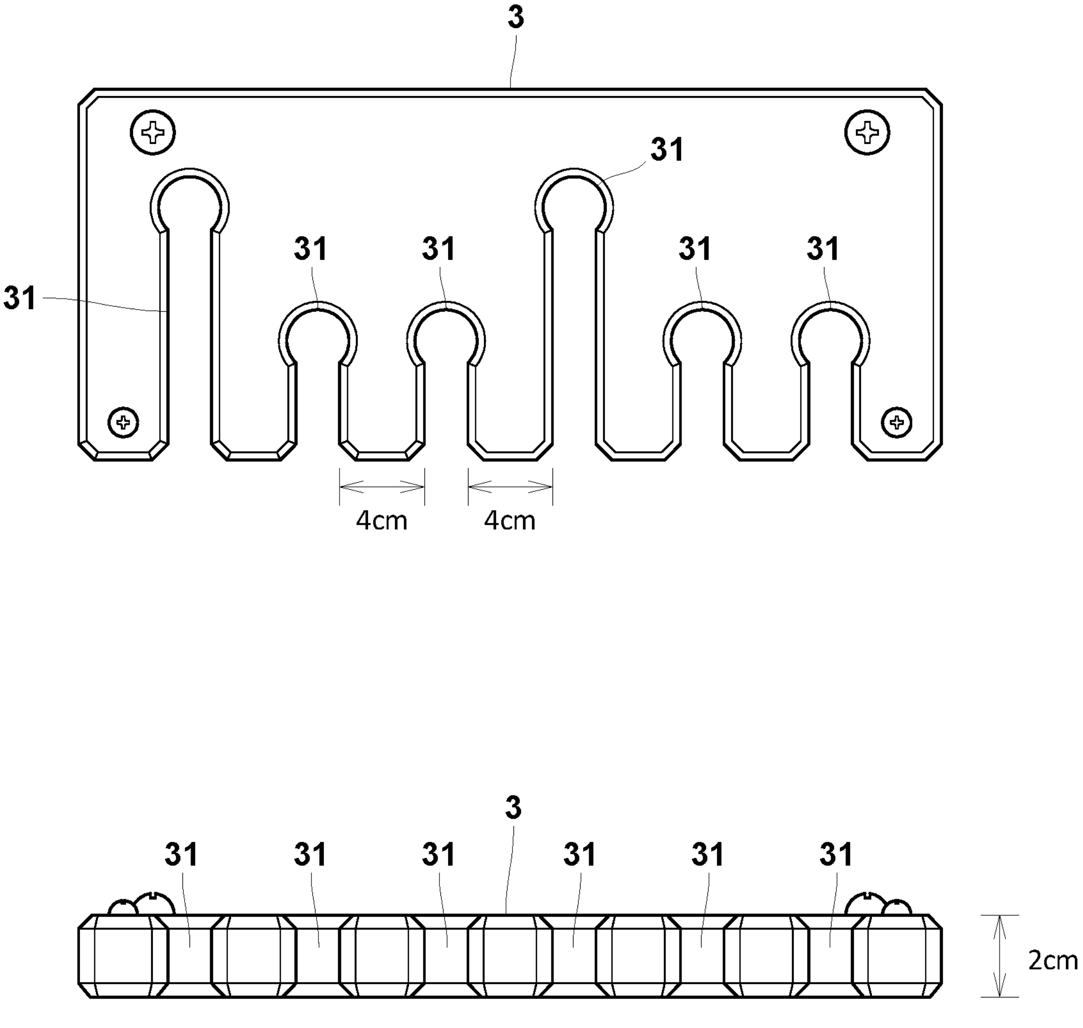
FIG. 6 is a plan view and a front view of a holding portion of the same embodiment.

The holding portion 3 holds the operation unit Z2 so that the operation unit Z2 does not fall off the endoscope cleaning cart 100 at the time of carrying. Specifically, as illustrated in FIG. 6, the holding portion 3 includes one or a plurality of hanger portions 31 for hooking the operation unit Z2.

Specifically, the holding portion 3 has a flat plate shape, and the plurality of hanger portions 31 into which the operation unit Z2 is inserted and hooked are formed from the front side portion (front side in the traveling direction) toward the rear. The holding portion 3 is provided above the upper extending portions 431 of the connecting frame portions 43*a* and 43*b*. That is, the holding portion 3 of the present embodiment is located above the handle portion 6.

Here, the plurality of hanger portions 31 are configured such that the operation units Z2 adjacent to each other are alternately arranged in a state where the plurality of operation units Z2 are hooked. Specifically, the hanger portions 31 formed rearward from the front side have different lengths. The interval between the hanger portions 31 (dimension between the hanger portions 31) is, for example, 4 cm from the size of the operation unit (scope head) of each company.

In addition, the holding portion 3 is formed of a material having translucency, and is formed using transparent resin in the present embodiment. Here, for example, a transparent acrylic plate having a thickness of 2 cm is used in order to impart durability to the holding portion 3.

Figure 7:
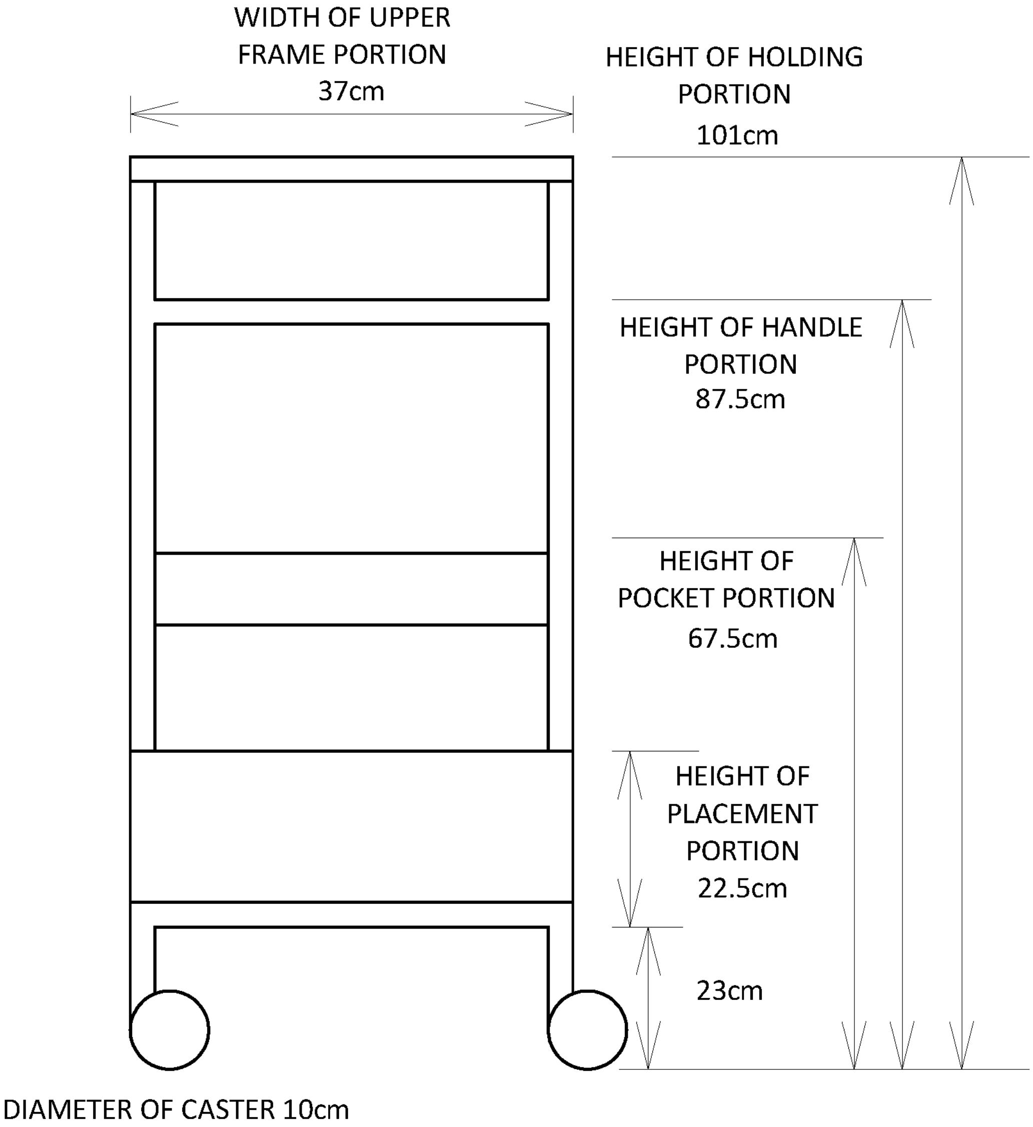
FIG. 7 is a schematic view illustrating dimensions of each unit of the endoscope cleaning cart of the embodiment.
Figure 8:
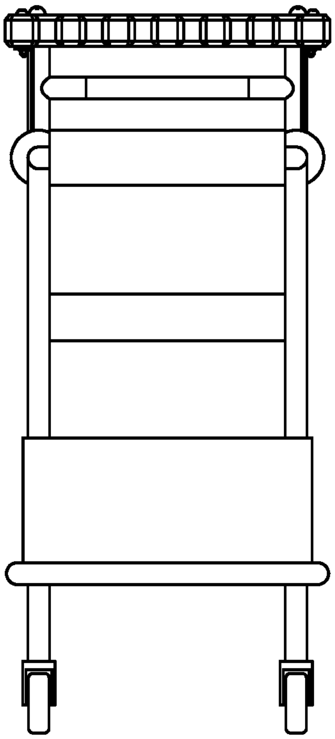
FIG. 8 is a front view of the endoscope cleaning cart of the present invention.
Figure 9:
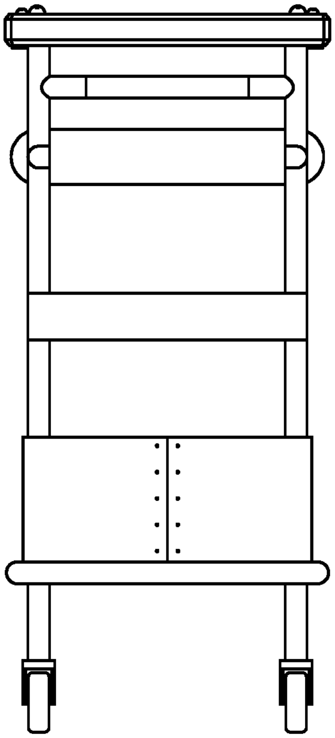
FIG. 9 is a rear view of the endoscope cleaning cart of the present invention.
Figure 10:
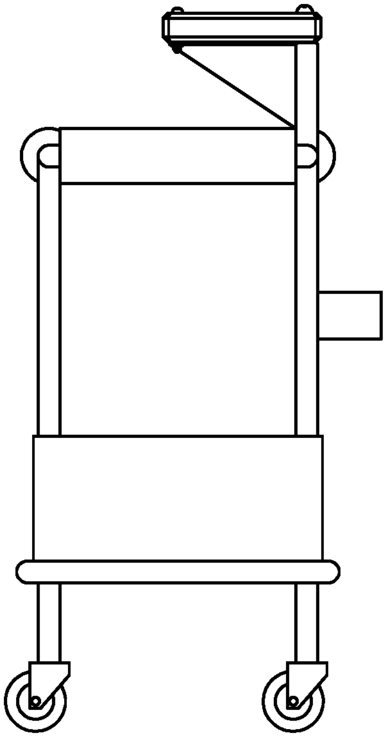
FIG. 10 is a right side view of the endoscope cleaning cart of the present invention.
Figure 11:
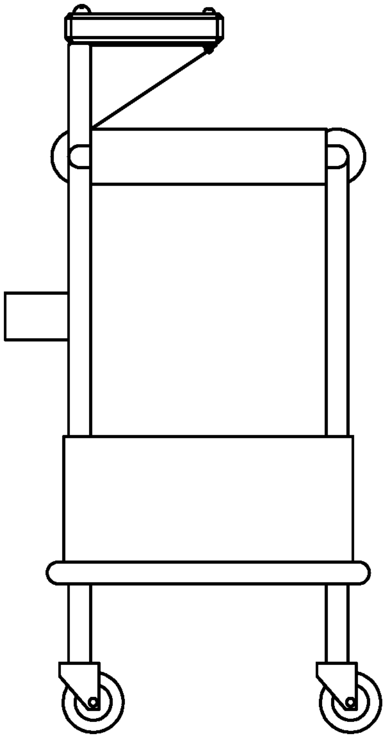
FIG. 11 is a left side view of the endoscope cleaning cart of the present invention.
Figure 12:
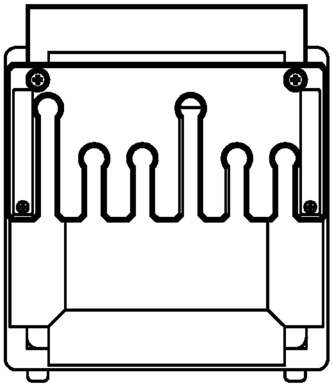
FIG. 12 is a plan view of the endoscope cleaning cart of the present invention.
Figure 13:
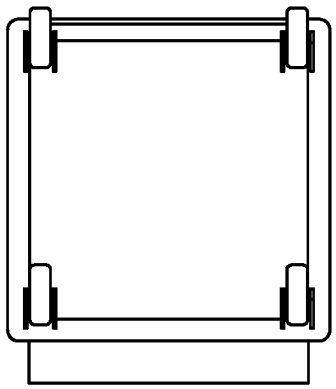
FIG. 13 is a bottom view of the endoscope cleaning cart of the present invention.

Finally, dimensions of each unit of the endoscope cleaning cart 100 of the present embodiment will be described with reference to FIG. 7.

The height dimension from the ground to the handle portion 6 of the endoscope cleaning cart 100 is 87.5 cm, and the height dimension to the ground of the holding portion 3 is 101 cm. These dimensions are set to heights that are easy to use in consideration of the average height of females of 155 cm (20 years old). In addition, in the cart main body 4, the front-rear dimension and the left-right dimension of the lower frame portion 41 are the same, and the front-rear dimension and the left-right dimension of the upper frame portion 42 are the same, and the width dimension (front-rear dimension) of the upper frame portion 42 is 37 cm. This width dimension is set to a dimension that improves the stability of the endoscope cleaning cart 100 as examined from JIS dimension standards of the wheelchair. Further, in consideration of stability, casters 5 having a diameter of 10 cm are used, and stoppers are provided on two casters 5 on a diagonal line. Other dimensions are as illustrated in FIG. 7.

Effects of Present Embodiment

According to the endoscope cleaning cart 100 of the present embodiment configured as described above, it is possible to efficiently perform the bedside cleaning of the endoscope Z by causing the holding portion 3 to hold the operation unit Z2 of the endoscope Z immediately after removal from the body cavity of the patient and immersing the insertion unit Z1 in the cleaning liquid in the storage bag B1. In addition, since the endoscope Z after use can be carried to the cleaning chamber in this state, it is possible to safely carry the endoscope Z after use and to efficiently clean the endoscope Z in the cleaning chamber.

OTHER EMBODIMENTS

For example, the holding portion 3 of the above embodiment has the hanger portion 31 for hooking the operation unit Z2, but may have a structure for holding the operation unit Z2 so as not to fall from the cart 100 at the time of carrying, such as a holding portion for sandwiching and holding the operation unit Z2.

In addition, although the holding portion 3 of the above embodiment is provided on the same side as the handle portion 6, the holding portion 3 may be provided on the opposite side (front side in the traveling direction) to the handle portion 6 in the cart main body 4, or may be provided on one of the left and right sides in the cart main body 4.

Further, in the above embodiment, the cushion member 7 is disposed in the leakage preventing box 8, but in the case of a configuration not including the leakage preventing box 8, the cushion member 7 may be provided in the placement portion 2.

The placement portion 2 is not limited to the configuration including the placement surface portion 21 and the side wall portion 22 as long as the storage bag B1 does not fall, and specifically, a recess for storing the storage bag B1 may be formed.

In addition, in the above embodiment, the casters are provided on the lower extending portions 432 of the connecting frame portion 43, but the casters 5 may be provided on the lower surface of the placement portion 2.

In addition, the cart main body has a substantially rectangular parallelepiped frame shape, but may have other shapes.

In addition, various modifications and combinations of the embodiment may be made without departing from the gist of the present invention.

LIST OF REFERENCE CHARACTERS

100 endoscope cleaning cart
Z endoscope
Z1 insertion unit
Z2 operation unit
B1 storage bag
B2 leakage preventing bag
2 placement portion
3 holding portion
31 hanger portion
4 cart main body
42 upper frame portion
43*a* to 43*d* connecting frame portion
6 handle portion
7 cushion member
8 leakage preventing box

INDUSTRIAL APPLICABILITY

According to the present invention, it is possible to provide a cart capable of performing bedside cleaning and carrying an endoscope.

The invention claimed is:

1. An endoscope cleaning cart that carries an endoscope including an insertion unit to be inserted into a body cavity and an operation unit for operating the insertion unit, the endoscope cleaning cart comprising:

a placement portion on which a storage bag storing a cleaning liquid is placed;

a holding portion that holds the operation unit above the placement portion; and a leakage preventing box that is provided between the storage bag and the placement portion and stores a lower portion of the storage bag, wherein the insertion unit is immersed in the cleaning liquid in the storage bag, and the leakage preventing box is set with a leakage preventing bag that stores the lower portion of the storage bag, and is detachably provided from the placement portion.

2. The endoscope cleaning cart according to claim 1, wherein the holding portion includes one or a plurality of hanger portions for hooking the operation unit.

3. The endoscope cleaning cart according to claim 2, wherein the plurality of hanger portions include adjacent hanger portions having different lengths in a predetermined direction such that the adjacent hanger portions are alternately arranged.

4. The endoscope cleaning cart according to claim 1, wherein the holding portion is formed of a material having translucency.

5. The endoscope cleaning cart according to claim 1, wherein a cushion member is provided below the storage bag in the placement portion.

6. The endoscope cleaning cart according to claim 1, further comprising a handle portion gripped at a time of conveying the endoscope cleaning cart to thereby carry the endoscope, the handle portion being provided on a rear side in a traveling direction, wherein the handle portion and the holding portion are provided on the same side.

7. An endoscope cleaning cart that carries an endoscope including an insertion unit to be inserted into a body cavity and an operation unit for operating the insertion unit, the endoscope cleaning cart comprising:

a placement portion on which a storage bag storing a cleaning liquid is placed;

a holding portion that holds the operation unit above the placement portion;

an upper frame portion to which an upper portion of the storage bag is attached; and a connecting frame portion provided between the upper frame portion and the placement portion, wherein the insertion unit is immersed in the cleaning liquid in the storage bag, and a space is formed between the upper frame portion and the placement portion.

* * * * *